United States Patent
Kim et al.

(10) Patent No.: US 11,160,755 B2
(45) Date of Patent: *Nov. 2, 2021

(54) AMPHIPHILIC POLYMER

(71) Applicants: LG CHEM, LTD., Seoul (KR); LG HOUSEHOLD & HEALTH CARE LTD., Seoul (KR)

(72) Inventors: Su Jeong Kim, Daejeon (KR); Jeong Ae Yoon, Daejeon (KR); Sun Hwa Lee, Daejeon (KR); Woo Sun Shim, Daejeon (KR); Sung Soo Yoon, Daejeon (KR); Chang Hwan Ju, Daejeon (KR); Kyung Oh Kim, Daejeon (KR); Jung A Kim, Daejeon (KR); Nae Gyu Kang, Daejeon (KR)

(73) Assignees: LG Chem, Ltd., Seoul (KR); LG Household & Health Care Ltd., Seoul (KR)

( * ) Notice: Subject to any disclaimer, the term of this patent is extended or adjusted under 35 U.S.C. 154(b) by 421 days.

This patent is subject to a terminal disclaimer.

(21) Appl. No.: 16/303,529

(22) PCT Filed: Jun. 16, 2017

(86) PCT No.: PCT/KR2017/006337
§ 371 (c)(1),
(2) Date: Nov. 20, 2018

(87) PCT Pub. No.: WO2017/217813
PCT Pub. Date: Dec. 21, 2017

(65) Prior Publication Data
US 2020/0323775 A1    Oct. 15, 2020

(30) Foreign Application Priority Data
Jun. 16, 2016 (KR) .................. 10-2016-0075036
Jun. 16, 2017 (KR) .................. 10-2017-0076508

(51) Int. Cl.
*A61K 9/107* (2006.01)
*A61K 31/353* (2006.01)
(Continued)

(52) U.S. Cl.
CPC .......... *A61K 9/1075* (2013.01); *A61K 31/353* (2013.01); *A61K 31/366* (2013.01);
(Continued)

(58) Field of Classification Search
CPC .. A61K 9/1075; A61K 31/353; A61K 31/366; A61K 31/575; A61K 47/32;
(Continued)

(56) References Cited

U.S. PATENT DOCUMENTS 6,491,903 B1    12/2002    Forster et al.
6,616,946 B1 *  9/2003    Meier .................. A61K 9/0009
                                                                424/489
(Continued)

FOREIGN PATENT DOCUMENTS

EP    1225873 B1    3/2006
EP    2729002 B1    8/2016

OTHER PUBLICATIONS

Nelson, C.E., et al. in ACS NANO, vol. 7, #10, 8870-8880, 2013.*
(Continued)

*Primary Examiner* — Gollamudi S Kishore
(74) *Attorney, Agent, or Firm* — Dentons US LLP

(57) ABSTRACT

The present application relates to an amphiphilic polymer and a method for producing the same. The present application also relates to micelles comprising the amphiphilic polymer and a method for producing the same. The amphiphilic polymer of the present application can have excellent dispersion properties while effectively encapsulating the drug.

20 Claims, 1 Drawing Sheet

(51) Int. Cl.
  *A61K 31/366*    (2006.01)
  *A61K 31/575*    (2006.01)
  *C08F 293/00*    (2006.01)
  *C08F 297/02*    (2006.01)

(52) U.S. Cl.
  CPC .......... *A61K 31/575* (2013.01); *C08F 293/00* (2013.01); *C08F 297/02* (2013.01)

(58) Field of Classification Search
  CPC ... A61K 9/5026; A61K 8/0291; C08F 293/00; C08F 297/02; C08F 2438/02; C08F 2438/03; C08F 293/005; C08F 2438/01; C08F 297/026; C08F 212/08; C08F 226/06; C08F 226/10; C08G 65/34; C08G 73/12
  See application file for complete search history.

(56) References Cited

U.S. PATENT DOCUMENTS

| | | |
|---|---|---|
| 6,916,488 B1 | 7/2005 | Meier et al. |
| 2007/0253899 A1* | 11/2007 | Ai .......................... A61K 47/62 424/1.37 |
| 2009/0069186 A1* | 3/2009 | Shirley .................. B01F 17/00 504/360 |
| 2016/0271062 A1 | 9/2016 | Lebouille et al. |
| 2018/0085318 A1 | 3/2018 | Steendam et al. |

OTHER PUBLICATIONS

Miteva, M., et al. in Biomaterials, vol. 38, 97-107, 2015.*
E.K. Pramod Kumar et al. "Cross-linked Self-Assembled Micelle Based Nanosensor for Intracellular pH Measurements";Journal of Materials Chemistry. B; 2014; pp. 6652-6659.

* cited by examiner

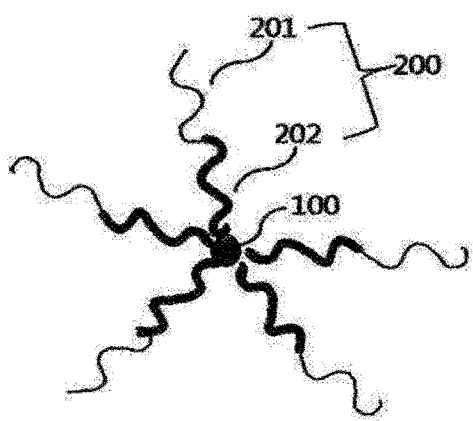

AMPHIPHILIC POLYMER

TECHNICAL FIELD

The present application relates to an amphiphilic polymer, a process for preparing the same, micelles comprising the amphiphilic polymer and a composition comprising the micelles. This application is a National Stage of International Application No. PCT/KR2017/006337 filed on Jun. 16, 2017, and claims the benefit of Korean Application No. 10-2016-0075036 filed on Jun. 16, 2016 and Korean Patent Application No. 10-2017-0076508 filed on Jun. 16, 2017, all of which are hereby incorporated by reference in their entirety for all purposes as if fully set forth herein.

BACKGROUND ART

In the field of pharmacy and cosmetics, there has been a demand for the development of dosage forms capable of effectively acting on the skin and improving the condition of the skin while stably collecting various substances having efficacy on the skin in the product.

However, most of drugs were poorly soluble or unstable to bind to or react with other substances, so that they did not exhibit the drugs' efficacy or there were difficulties in formulation.

Accordingly, various techniques have been developed for more stably and easily collecting a potent drug in a dosage form, and for example, can be exemplified by nanoemulsions in which emulsion particles are prepared in nano units, liposomes using self-assembly characteristics of phospholipids, solid lipid nanoparticles in which solid lipids are nano-particulated or polymeric nanoparticles in which interfaces are stabilized with a surfactant, and the like.

However, these nanoparticles have still suffered from the difficulty in improving the percutaneous absorption effect depending on the poor solubility problem and the dispersion characteristics of the target drug.

DISCLOSURE

Technical Problem

The present application provides an amphiphilic polymer capable of having excellent dispersion characteristics while effectively encapsulating a drug, and a method for producing the same.

The present application also provides micelles comprising an amphiphilic polymer, which are effectively dispersed in oil or in water and are capable of exhibiting excellent percutaneous absorption properties, and a composition comprising the micelles.

The above and other objects of the present application can be all attained by the present application which is described in detail below.

Technical Solution

In one example related to the present application, the present application relates to an amphiphilic polymer. The amphiphilic polymer according to the present application is a block copolymer capable of exhibiting phase separation characteristics, which can effectively encapsulate a drug using self-assembly characteristics and can also be included in a pharmaceutical composition or a cosmetic composition, and the like, under a state of having good dispersion properties.

In the present application, the term "amphiphilic polymer" means a polymer simultaneously containing regions having different physical properties, for example, different solubility parameters, which may mean, for example, a polymer containing a hydrophilic region and a hydrophobic region at the same time.

In the present application, the term "hydrophilic or hydrophobic region" means a region contained in a polymer, in such a state that it can be confirmed that each region is phase-separated, for example, while forming a block, where each degree of hydrophilicity or hydrophobicity is relative.

In the present application, the term "self-assembly characteristic" means a phenomenon that the amphiphilic block polymer spontaneously undergoes fine phase separation in oil or in water and has constant size regularity.

The amphiphilic polymer according to the present application comprises a first block (A) and a second block (B) phase-separated from the first block (A). Also, the second block (B) comprises a polymerized unit (B1) of a polymerizable monomer satisfying Formula 1 below and a polymerized unit (B2) of an acrylic monomer or vinyl monomer having a solubility parameter of a single polymer of less than 10 $(cal/cm^3)^{1/2}$.

[Formula 1]

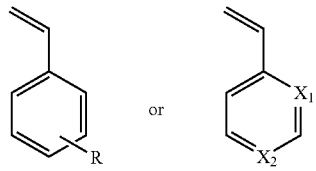

In Formula 1, R is hydrogen, a functional group capable of forming a hydrogen bond, or an alicyclic hydrocarbon group or aromatic substituent group comprising a functional group capable of forming a hydrogen bond, where said functional group can be at least one selected from the group consisting of a hydroxyl group, an amine group, a nitro group, an imide group, an alkoxysilane group and a cyano group, and X1 and X2 are each independently carbon or nitrogen.

The amphiphilic polymer of the present application can effectively collect a target material, for example, drugs to be described below, by comprising two blocks that are phase-separated from each other.

In the present application, the term "phase-separated from each other" means a state where the first block and the second block do not mix with each other and form the respective blocks in the absence of external action.

The first block (A) means a hydrophilic region of an amphiphilic polymer, which may comprise, for example, a polymer having a solubility parameter of 10 $(cal/cm^3)^{1/2}$ or more.

The method of obtaining the solubility parameter is not particularly limited and may be followed in a manner known in this field. For example, the parameter may be calculated or obtained according to a method known in the art as a so-called HSP (Hansen solubility parameter).

In another example, the first block (A) may comprise a polymer having a solubility parameter of 13 $(cal/cm^3)^{1/2}$ or more, 14 $(cal/cm^3)^{1/2}$ or more, 15 $(cal/cm^3)^{1/2}$ or more, 16 $(cal/cm^3)^{1/2}$ or more, or 17 $(cal/cm^3)^{1/2}$ or more. The upper limit of the solubility parameter of the first block (A) is not particularly limited, and may be, for example, 25 $(cal/cm^3)^{1/2}$ or less, or 23 $(cal/cm^3)^{1/2}$ or less.

The first block (A) satisfies the solubility parameter as described above and any known polymer can be included as long as it can form a hydrophilic region of an amphiphilic polymer capable of comprising a drug according to the present application.

In one example, the first block (A) may be any one selected from the group consisting of polyethylene glycol, a polyethylene glycol-propylene glycol copolymer, polyvinyl pyrrolidone and polyethyleneimine.

Specifically, the first block (A) may be polyethylene glycol having a number average molecular weight in a range of 500 to 100,000, but is not limited thereto. In the present application, the term "number average molecular weight" may mean an analytical value measured by a magnetic resonance apparatus (NMR), and unless otherwise specified, a molecular weight of any polymer may mean a number average molecular weight of the polymer.

In one example, the second block (B) comprises a polymerized unit (B1) of a polymerizable monomer satisfying Formula 1 below and a polymerized unit (B2) of an acrylic monomer or vinyl monomer having a solubility parameter of a single polymer of less than 10 $(cal/cm^3)^{1/2}$.

[Formula 1]

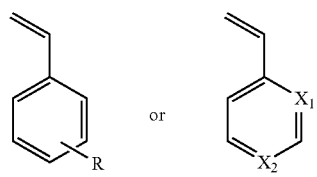

In the present application, the term "acrylic monomer" means (meth)acrylic acid or a derivative thereof. In addition, the term "(meth)acrylic acid" means acrylic acid or methacrylic acid.

As described below, the second block (B) of the amphiphilic polymer in the present application is a site for surrounding the drug adjacent to it and playing a role of forming a micelle shape as a whole.

Therefore, the second block (B) means a relatively hydrophobic site in the amphiphilic polymer.

As the polymerized unit (B1) of the polymerizable monomer satisfying Formula 1 above and the polymerized unit (B2) of the acrylic monomer or vinyl monomer, as described above, are simultaneously included in the second block (B), the amphiphilic polymer of the present application can improve collection ability of the target drug and position the drug more stably inside the micelles (core).

In Formula 1, wherein, R is hydrogen, a functional group capable of forming a hydrogen bond, or an alicyclic hydrocarbon group or aromatic substituent group comprising a functional group capable of forming a hydrogen bond, where said functional group can be at least one selected from the group consisting of a hydroxyl group, an amine group, a nitro group, an imide group, an alkoxysilane group and a cyano group, but not limited thereto. In Formula 1, X1 and X2 are each independently carbon or nitrogen.

The functional group capable of forming a hydrogen bond is not limited as long as it is a functional group which interacts with —H in a drug to be described below, and more specifically, forms a hydrogen bond to improve the collection ability of the drug and plays a role of an electron donor capable of positioning the drug more stably inside the micelles (core).

The polymerizable monomer comprising a functional group capable of forming a hydrogen bond can be exemplified by, for example, N,N-dimethyl-3-vinylaniline, 3-vinylaniline, 4-(3-vinylphenyl)pyridine, 3-vinylbenzoic acid, 2-vinylpyridine, 4-vinylpyridine, and the like, but is not limited thereto.

EXAMPLES

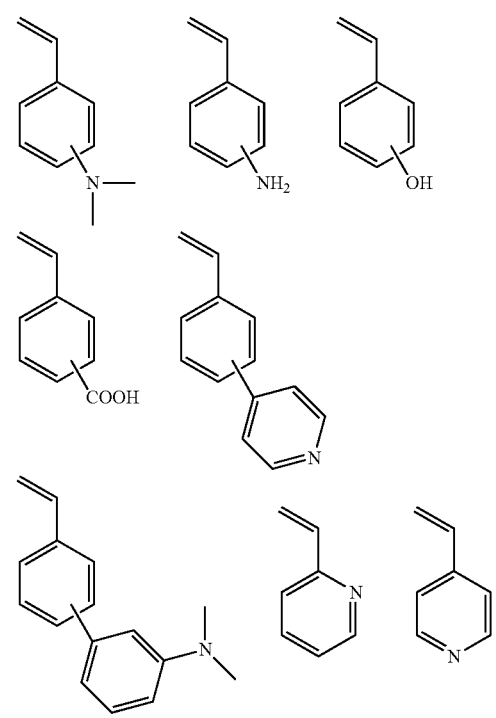

Such a polymerizable monomer of Formula 1 having a functional group capable of forming a hydrogen bond forms a polymerized unit (B1) in the second block (B), where the polymerized unit (B1) can perform the role of collecting the drug, for example, by being located outside the polymer.

The aromatic structure included in Formula 1 above can collect the drug to be described below efficiently, since π-π attraction forces act thereon with the aromatic structure of the drug.

Also, the second block (B) may comprise the polymerized unit (B1) of a polymerizable monomer satisfying Formula 1 and the polymerized unit (B2) of an acrylic monomer or vinyl monomer as described above in a predetermined weight ratio.

For example, the weight ratios (B1:B2) of the polymerized unit (B1) of the polymerizable monomer satisfying the structure of Formula 1 and the polymerized unit (B2) of the acrylic monomer or the vinyl monomer having a solubility parameter of a single polymer of less than 10.0 $(cal/cm^3)^{1/2}$ in the second block (B) may be the same or different. For example, the weight ratio (B1:B2) may be in a range of 0.5:99.5 to 50:50. In another example, the weight ratio (B1:B2) may be in the range of 10:90 to 30:70, 20:80 to 40:60, or 30:70 to 50:50. Within the range of such a weight ratio (B1:B2), it is possible to effectively collect the drug and to form the amphiphilic polymer safely dispersed in the aqueous solution.

In another example, the second block (B) may comprise a polymerized unit (B2) of an acrylic monomer or vinyl monomer having a solubility parameter of a single polymer of less than 9.8 $(cal/cm^3)^{1/2}$ or less than 9.5 $(cal/cm^3)^{1/2}$. The lower limit of the solubility parameter of the acrylic monomer or vinyl monomer is not particularly limited and may be, for example, 2 $(cal/cm^3)^{1/2}$ or more, or 4 $(cal/cm^3)^{1/2}$ or more.

The acrylic monomer can be exemplified by a compound represented by Formula 2 or 3 below, but is not limited thereto.

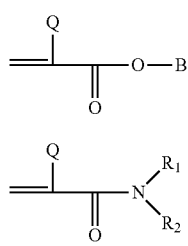

[Formula 2]

[Formula 3]

In Formulas 2 and 3, Q is hydrogen or an alkyl group, and B in Formula 1 is a linear or branched alkyl group, an alicyclic hydrocarbon group, an aromatic substituent group or a carboxyl group, having at least 1 carbon atom and R1 and R2 in Formula 3 are each independently hydrogen, or a linear or branched alkyl group, an alicyclic hydrocarbon group or an aromatic substituent group, having at least 1 carbon atom.

In Formulas 2 and 3, as the alkyl group present in Q, an alkyl group having 1 to 20 carbon atoms, 1 to 16 carbon atoms, 1 to 12 carbon atoms, 1 to 8 carbon atoms or 1 to 4 carbon atoms may be used. The alkyl group may be linear, branched or cyclic. In addition, the alkyl group may be optionally substituted with one or more substituents.

In Formulas 2 and 3, B, R1 and R2 may be each independently a linear or branched alkyl group having at least 1 carbon atom, at least 3 carbon atoms, at least 5 carbon atoms, at least 7 carbon atoms, or at least 9 carbon atoms, which may be optionally substituted or in a un-substituted state. Such a compound comprising a relatively long chain alkyl group is known as a hydrophobic compound. The upper limit of the carbon number in the linear or branched alkyl group is not particularly limited, and for example, may be an alkyl group having at most 20 carbon atoms.

In another example, B, R1 and R2 in Formulas 2 and 3 may be an alicyclic hydrocarbon group, for example, an alicyclic hydrocarbon group having 3 to 20 carbon atoms, 3 to 16 carbon atoms, or 6 to 12 carbon atoms, where an example of such a hydrocarbon group may be exemplified by an alicyclic alkyl group having 3 to 20 carbon atoms, 3 to 16 carbon atoms or 6 to 12 carbon atoms, such as a cyclohexyl group or an isobornyl group. Such a compound having an alicyclic hydrocarbon group is also known as a relatively hydrophobic compound.

In another example, B, R1 and R2 in Formulas 2 and 3 may be an aromatic substituent group, such as an aryl group or an arylalkyl group.

Here, the aryl group may be, for example, an aryl group having 6 to 24 carbon atoms, 6 to 18 carbon atoms, or 6 to 12 carbon atoms. The alkyl group of arylalkyl may be, for example, an alkyl group having 1 to 20 carbon atoms, 1 to 16 carbon atoms, 1 to 12 carbon atoms, 1 to 8 carbon atoms, or 1 to 4 carbon atoms. The aryl group or arylalkyl group may be exemplified by a phenyl group, a phenylethyl group, a phenylpropyl group or a naphthyl group, but is not limited thereto.

In the present application, the substituent which may optionally be substituted in the alkyl group, aryl group or hydrocarbon group, and the like in Formulas 2 and 3 above may be exemplified by halogen such as chlorine or fluorine, an epoxy group such as a glycidyl group, an epoxyalkyl group, a glycidoxyalkyl group or an alicyclic epoxy group, an acryloyl group, a methacryloyl group, an isocyanate group, a thiol group, an alkyl group, an alkenyl group, an alkynyl group or an aryl group, and the like, but is not limited thereto.

The compound represented by Formula 2 above may be, for example, alkyl (meth)acrylate. Here, the term "(meth)acrylate" means acrylate or methacrylate. The alkyl (meth)acrylate may be exemplified by, for example, methyl (meth)acrylate, ethyl (meth)acrylate, n-propyl (meth)acrylate, isopropyl (meth)acrylate, n-butyl (meth)acrylate, t-butyl (meth)acrylate, sec-butyl (meth)acrylate, pentyl (meth)acrylate, hexyl (meth)acrylate, 2-ethylhexyl (meth)acrylate, 2-ethylbutyl (meth)acrylate, n-octyl (meth)acrylate, isobornyl (meth)acrylate, isooctyl (meth)acrylate, isononyl (meth)acrylate or lauryl (meth)acrylate, and the like, but is not limited thereto.

In the present application, among the monomers as above, an appropriate type may be selected and used in consideration of physical properties of the desired amphiphilic polymer.

In one example, in Formula 2, Q may be hydrogen or an alkyl group having 1 to 4 carbon atoms, and B may be an alkyl group having 7 or more carbon atoms or an alicyclic hydrocarbon group having 6 to 12 carbon atoms, without being limited thereto.

The second block (B) may comprise a polymerized unit (B2) of a vinyl monomer having a solubility parameter of a single polymer of less than 10 $(cal/cm^3)^{1/2}$, where the vinyl monomer may be a compound represented by Formula 4 or 5 below.

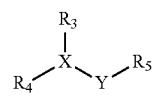

[Formula 4]

In Formula 4, X is a nitrogen atom or an oxygen atom, Y is a carbonyl group or a single bond, R3 and R5 are each independently hydrogen or an alkyl group, or R3 and R5 are linked together to form an alkylene group, and R4 is an alkenyl group (provided that when X is an oxygen atom, R3 is not present).

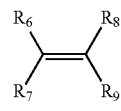

[Formula 5]

In Formula 5, R6, R7 and R8 are each independently hydrogen or an alkyl group, and R9 is a cyano group or an aromatic substituent group.

When Y in Formula 4 is a single bond, a structure in which no separate atom is present in the moiety represented by Y and R5 and X are directly linked can be realized.

In Formula 4, R4 may be, for example, a linear, branched or cyclic alkenyl group having 2 to 20 carbon atoms, 2 to 16 carbon atoms, 2 to 12 carbon atoms, 2 to 8 carbon atoms or 2 to 4 carbon atoms, which may be in an optionally substituted or un-substituted state. Generally, as the alkenyl group, a vinyl group or an allyl group, and the like may be used.

In Formula 4, R3 and R5 may be each independently hydrogen or a linear, branched or cyclic alkyl group having 1 to 20 carbon atoms, 1 to 16 carbon atoms, 1 to 12 carbon atoms, 1 to 8 carbon atoms, or 1 to 4 carbon atoms, or linked together to form an alkylene group having 1 to 20 carbon atoms, 2 to 16 carbon atoms, 2 to 12 carbon atoms, or 2 to 8 carbon atoms. Here, when R3 and R5 form an alkylene group, the compound of Formula 4 may be a cyclic compound.

The vinyl monomer represented by Formula 4 or 5 above may be exemplified by, for example, a styrene-based monomer such as styrene or methyl styrene; acrylonitrile; an amide-based monomer such as an N-vinylamide compound; an ester-based monomer such as a vinyl ester compound; or an ether-based monomer such as a vinyl ether compound, but is not limited thereto and it can be used as a vinyl monomer contained as a polymerized unit in the amphiphilic polymer of the present application without limitation as long as it satisfies the solubility parameter of the single polymer as described above.

The second block (B) may, for example, have a number average molecular weight in the range of 500 to 100,000. Within such a range, desired hydrophobic properties and collection ability of drugs can be secured.

In one example, the amphiphilic polymer may have a different block ratio (A:B) of the first block (A) and the second block (B).

Specifically, the amphiphilic polymer of the present application can adjust the block ratio (A:B) of the first block (A) and the second block (B) within the range of 1:9 to 9:1. Here, the term "block ratio (A:B)" means a mass ratio between the respective blocks.

In another example, the block ratio (A:B) of the first block (A) and the second block (B) may be 2:8 to 8:2, 3:7 to 7:3, or 4:6 to 6:4.

The amphiphilic polymer may have a number average molecular weight (Mn) in the range of 1,000 to 500,000.

In another example related to the present application, the present application relates to micelles. The micelles according to the present application may comprise the above-described amphiphilic polymer.

In the present application, the term "micelle" may mean a particle of a size from several nanometers to tens of thousands nanometers having a core/shell structure by self-assembly characteristics of an amphiphilic polymer.

The micelles comprising the amphiphilic polymer of the present application can have excellent dispersion properties in oil or in water and can also have excellent stability.

Such micelles may further comprise, for example, a drug encapsulated by an amphiphilic polymer.

In one example, as shown in FIG. 1, the micelle of the present application may be a structure comprising a drug (100) and an amphiphilic polymer (200) encapsulating the drug (100). The amphiphilic polymer (200) may comprise a first block (201) and a second block (202), where the second block (202) of the amphiphilic polymer (200) may have a structure adjacent to the drug (100). Here, the encapsulation is a term meaning a structure in which an amphiphilic polymer surrounds a drug, as in FIG. 1, which is used in the present application in the same meaning as "collection."

Typically, the drug is poorly soluble, but the drug of the present application is encapsulated by an amphiphilic polymer having both a hydrophobic region and a hydrophilic region, thereby ensuring excellent dispersion characteristics of the drug in oil or in water.

Also, in the case of the micelles of the present application, they may comprise the amphiphilic polymer having the same or different block ratio (A:B) of the first block (A) and the second block (B), thereby further securing the superiority of the above-described dispersion characteristics, and further comprise a functional group capable of performing a predetermined interaction with the drug, thereby having an excellent encapsulation characteristic.

The drug contained in the micelles of the present application is not particularly limited, but may comprise, for example, a physiologically active substance.

In one example, the physiologically active material may be poorly soluble.

Such a physiologically active substance may be, for example, any one selected from the group consisting of genistein, daidzein, prangenidin or a derivative thereof; polyphenols; or a mixture thereof.

The genistein, daidzein, prangenidin or a derivative thereof as one example of the physiologically active substance means a phenolic compound or its glycoside contained in soybean, which has a similar structure to estrogen of a female hormone, and has an excellent antioxidant effect or the like and thus is used in various fields from skin care to anticancer therapy.

Isoflavone such as genistein, daidzein, cucurbitacin, prangenidin or a derivative thereof is a phenolic compound, which comprises intra-molecular hydrogen (—H), where the intra-molecular hydrogen is subjected to a hydrogen bond with the functional group that the hydrogen bond is possible, which is included in the second block (B) of the amphiphilic polymer, whereby the stability of the drug positioned inside the micelles can be improved.

Specifically, the isoflavone may be genistein or a glycoside of the genistein, for example, acetyl genistein or malonyl genistein, and the like, but is not limited thereto.

The drug contained in the micelles may be included in the micelles in such an amount to be capable of expressing the physiological activity when the micelles have been prepared into a dosage form.

In one example, the drug content may be in a range of 1 to 60 wt %, 1 to 50 wt %, 1 to 40 wt %, or 1 to 20 wt %, relative to the total weight of the micelles. If the drug content is more than 60 wt %, effective collection may not be achieved, and the drug may flow out of the micelles to be aggregated into a crystalline form or modified.

Such micelles may have an average particle diameter, for example, in a range of 1 nm to 10,000 nm. The average particle diameter of the micelles is a value measured by a dynamic light scattering method, which may be a range covering a particle diameter of a single micelle or micelle aggregates themselves.

In another embodiment related to the present application, the present application relates to a composition comprising micelles. The composition according to the present application may be a composition for producing particles comprising micelles containing the amphiphilic polymer.

The composition for producing particles of the present application comprises micelles formed due to self-assembly characteristics of an amphiphilic polymer. In addition, the amphiphilic polymer forming such micelles may be encapsulating, for example, a drug.

More specifically, the micelles contained in the composition for producing particles may further comprise an amphiphilic polymer and a drug encapsulated by the amphiphilic polymer.

The present application also relates to a pharmaceutical or cosmetic composition comprising micelles comprising the amphiphilic polymer. Specifically, the micelles contained in the pharmaceutical or cosmetic composition may comprise an amphiphilic polymer and a drug encapsulated by the amphiphilic polymer.

In one example, when the composition is a pharmaceutical composition, the drug in the micelle may be included in the composition in a pharmaceutically acceptable form. In addition, the pharmaceutical compositions may be in various dosage forms such as oral or parenteral dosage forms.

When the pharmaceutical composition is formulated, it may be prepared using diluents or excipients such as a filling agent, an extender, a binder, a wetting agent, a disintegrant or a surfactant, as usually used.

In one example, solid formulations for oral administration include tablets, pills, powders, granules or capsules, and the like, where such a solid formulation may be prepared by mixing at least one compound with at least one or more of excipients, for example, starch, calcium carbonate, sucrose or lactose, gelatin and the like.

In one example, liquid formulations for oral administration include suspensions, content solutions, emulsions or syrups, and the like, and in addition to water or liquid paraffin, which is a simple diluent commonly used, various excipients, for example, a wetting agent, a sweetener, a refresher or a preservative, and the like may be included. Formulations for parenteral administration may include sterile aqueous solutions, non-aqueous solvents, suspensions, emulsions, lyophilized formulations, or suppositories.

The pharmaceutical composition may be formulated into any form suitable for pharmaceutical formulations, including oral dosage forms such as powders, granules, tablets, capsules, suspensions, emulsions, syrups or aerosols; external preparations such as ointments or creams; suppositories; or sterile injectable solutions, and the like, and used.

In another example, the composition may be a cosmetic composition that may be included in skin external preparations having dosage forms such as emollients, astringent lotions, nourishing creams, cleansing foams, essences or packs.

In the cosmetic composition and the skin external preparation, a known additive component such as a powder base or a carrier (a binder, a disintegrant, an excipient or a lubricant, and the like), an oil base or a carrier (animal and plant oils, waxes, Vaseline, paraffin oils, silicone oils, higher fatty acid esters or higher fatty acids, and the like), an aqueous base or a carrier (gel base such as xanthan gum, and the like), a preservative, a chelating agent, an antioxidant, a refrigerant, a stabilizer, a fluidizing agent, an emulsifier, a viscosifying agent, a buffering agent, a dispersant, an adsorbent, a humectant, a wetting agent, a desiccant, an antistatic agent or other resins (an olefin resin such as a polyamide resin hydrogenated polybutene), and the like may be included.

In one example, the pharmaceutical composition or cosmetic composition may be in a form of a water-in-oil or oil-in-water emulsion.

Micelles in the composition may, for example, form aggregates. Such micelle aggregates may be formed due to van der Waals force between hydrophobic regions. The size of such micelle aggregates may be, for example, in a range of 10 nm to 10,000 nm.

In another example according to the present application, the present application relates to a method for producing an amphiphilic polymer according to the present application. The production method according to the present application may comprise a step of polymerizing a polymer forming a first block (A), and a polymerized unit (B1) of a polymerizable monomer satisfying Formula 1 and an acrylic monomer or vinyl monomer (B2) having a solubility parameter of a single polymer of less than 10.0 $(cal/cm^3)^{1/2}$, forming a second block (B).

Specifically, in the step of producing the amphiphilic polymer, the method of polymerizing the polymer forming the first block (A) and the above-described monomers is not particularly limited, but for effectively attaining a narrow molecular weight distribution and the desired molecular weight, living radical polymerization, for example, atom transfer radical polymerization (ATRP) can be used.

More specifically, the amphiphilic polymer of the present application may be produced by reacting the polymer of the first block (A) containing halogen atoms with a transition metal complex catalyst to produce radicals and forming the second block (B) while being polymerized from double bond sites of the monomer for forming the second block through the radicals, but is not limited thereto.

The polymer forming the first block (A) is, for example, a polymer having a solubility parameter of 10.0 $(cal/cm^3)^{1/2}$ or more with or without any halogen atom, where if the polymer for forming the first block (A) without any halogen atom is used, the method may further comprise a step of preparing an initiator for ATRP through the reaction with a compound comprising a halogen atom.

In another example according to the present application, the present application relates to a method for producing micelles comprising a step of mixing the amphiphilic polymer thus prepared with a drug.

For preparing the micelles, the method of mixing the amphiphilic polymer and the drug is not particularly limited, and for example, may comprise dissolving the amphiphilic polymer in a predetermined organic solvent, for example, ethanol or the like, and then mixing the prepared solution and a solution comprising a drug.

Furthermore, the method may comprise a process of removing the solvent as a subsequent process after the process without being limited thereto and known additional processes may be involved between the respective processes or as subsequent processes.

The temperature in the process of removing the solvent differs depending on the boiling point of each solvent, and for example, the solvent may be removed at a temperature of 50° C. or higher, without being limited thereto.

Advantageous Effects

The present application can provide an amphiphilic polymer capable of effectively encapsulating a drug and having an excellent dispersion property on an aqueous solution, and a method for producing the same.

The present application can provide micelles which are effectively dispersed in oil or in water and can exhibit excellent percutaneous absorption characteristics upon preparation into a dosage form, and a composition comprising the same.

BRIEF DESCRIPTION OF DRAWINGS

FIG. 1 is a schematic diagram of a micelle comprising an amphiphilic polymer according to the present application.

MODE FOR INVENTION

Hereinafter, the present application will be described in more detail by way of examples, but the examples are merely examples limited to the gist of the present application. Furthermore, it is obvious to those skilled in the art that the present application is not limited to the process conditions set forth in the following examples and they may be optionally selected within the scope of the conditions necessary for achieving the object of the present application.

Example 1: Production of Amphiphilic Polymer (P1)

After dissolving a polyethylene glycol monomethyl ether (mPEG-OH) polymer (molecular weight: 5,000, manufacturer: Aldrich) forming the first block in dichloromethane at a concentration of 30%, 3 equivalents of triethylamine and 2 equivalents of 2-bromoisobutyryl bromide relative to the —OH functional group are added thereto and reacted to prepare an initiator for ATRP. Thereafter, a process of precipitation and collection in a solvent of diethyl ether is repeated twice and dried to obtain a bromine-terminal polyethylene glycol polymer from which impurities have been removed. 100 parts by weight of the obtained bromine-terminal polyethylene glycol polymer was dissolved in 250 parts by weight of an anisole reaction solvent on a flask and 17 parts by weight of styrene (solubility parameter: 8.7 $(cal/cm^3)^{1/2}$, B1) and 154 parts by weight of methyl methacrylate (solubility parameter: 9.5 $(cal/cm^3)^{1/2}$, B2) were introduced and the flask was sealed with a rubber stopper. Thereafter, the dissolved oxygen was removed through nitrogen purging and stirring at room temperature for 30 minutes, the flask was immersed in an oil bath set at 60° C., and the reaction was carried out by introducing a cupric bromide complex and a catalyst reducing agent. When the desired molecular weight was prepared, the reaction was terminated to prepare an amphiphilic polymer (P1). The molecular weight and the block ratio (A:B) of the amphiphilic polymer (P1) and the weight ratio (B1:B2) of the polymerized units in the second block (B) are shown in Table 1 below.

Example 2: Production of Amphiphilic Polymer (P2)

After dissolving a polyethylene glycol monomethyl ether (mPEG-OH) polymer (molecular weight: 5,000, manufacturer: Aldrich) forming the first block in dichloromethane at a concentration of 30%, 1.5 equivalents of 4-cyano-4-[(dodecylsulfanylthiocarbonyl)sulfanyl]pentanoic acid and 1.5 equivalents of 1,3-dicyclohexyl carbodiimide and 1.5 equivalents of 4-(dimethylamino)pyridine relative to the —OH functional group are added thereto and reacted to prepare an initiator for RAFT. Thereafter, a process of precipitation and collection in a solvent of diethyl ether is repeated twice and dried to obtain an RAFT agent-terminal polyethylene glycol polymer from which impurities have been removed. The obtained RAFT agent-terminal polyethylene glycol monomethyl ether polymer was dissolved in an anisole reaction solvent on a flask and N,N-dimethyl vinylbenzyl amine (B1):methyl methacrylate (solubility parameter: 9.5 $(cal/cm^3)^{1/2}$, B2) were introduced in a weight ratio of 10:90 and the flask was sealed with a rubber stopper. Thereafter, the dissolved oxygen was removed through nitrogen purging and stirring at room temperature for 30 minutes, the flask was immersed in an oil bath set at 60° C., and the reaction was carried out by introducing AIBN. When the desired molecular weight was prepared, the reaction was terminated to prepare an amphiphilic polymer (P2). The molecular weight and the block ratio (A:B) of the amphiphilic polymer (P2) and the weight ratio (B1:B2) of the polymerized units in the second block (B) are shown in Table 1 below.

Example 3: Production of Amphiphilic Polymer (P3)

2.5 parts by weight of NaH relative to 5 parts by weight of TEMPO ((2,2,6,6-tetramethyl-piperidin-1-yl)oxyl) is dissolved in DMF (dimethylformaldehyde) at a concentration of 10%, stirred for 1 hour under reflux, and then 100 parts by weight of a bromine-terminal polyethyleneglycol monomethylether (prepared in Example 1) polymer dissolved in DMF (dimethylformaldehyde) at a concentration of 20% is dropped. After stirring for 24 hours under reflux, the excess amount of NaH is removed by dropping methanol, and then a process of precipitation and collection in a solvent of diethyl ether is repeated twice and dried to obtain an alkoxy amine-terminal polyethylene glycol polymer from which impurities have been removed. The above-prepared alkoxy amine-terminal polyethyleneglycol monomethyl ether polymer was dissolved in an anisole reaction solvent on a flask and 4-(3-vinylphenyl)pyridine (B1): methyl methacrylate (solubility parameter: 9.5 $(cal/cm^3)^{1/2}$, B2) were introduced in a weight ratio of 30:70 and the flask was sealed with a rubber stopper. Thereafter, the dissolved oxygen was removed through nitrogen purging and stirring at room temperature for 30 minutes, the flask was immersed in an oil bath set at 120° C., and the reaction was carried out. When the desired molecular weight was prepared, the reaction was terminated to prepare an amphiphilic polymer (P1). The molecular weight and the block ratio (A:B) of the amphiphilic polymer (P1) and the weight ratio (B1:B2) of the polymerized units in the second block (B) are shown in Table 1 below.

Example 4: Production of Amphiphilic Polymer (P4)

After dissolving a polyethylene glycol monomethyl ether polymer (molecular weight: 5,000, manufacturer: Aldrich) forming the first block in dichloromethane at a concentration of 30%, 1.5 equivalents of 4-cyano-4-[(dodecylsulfanylthiocarbonyl)sulfanyl]pentanoic acid and 1.5 equivalents of 1,3-dicyclohexyl carbodiimide and 1.5 equivalents of 4-(dimethylamino)pyridine relative to the —OH functional group are added thereto and reacted to prepare an initiator for RAFT. Thereafter, a process of precipitation and collection in a solvent of diethyl ether is repeated twice and dried to obtain an RAFT agent-terminal polyethylene glycol polymer from which impurities have been removed. The obtained RAFT agent-terminal polyethylene glycol monomethyl ether polymer was dissolved in an anisole reaction solvent on a flask and styrene (B1): methyl methacrylate (solubility parameter: 9.5 $(cal/cm^3)^{1/2}$, B2) were introduced in a weight ratio of 50:50 and the flask was sealed with a rubber stopper. Thereafter, the dissolved oxygen was removed through nitrogen purging and stirring at room temperature for 30 minutes, the flask was immersed in an oil bath set at 80° C., and the reaction was carried out by introducing AIBN. When the desired molecular weight was prepared, the reaction was terminated to prepare an amphiphilic polymer.

Comparative Example 1: Production of Amphiphilic Polymer (P5)

Polyethylene glycol monomethyl ether polymer (molecular weight: 5000, manufacturer: Aldrich) forming the first block was dried in Sn(Oct)$_2$ and 2-neck round flask at 110° C. under vacuum for 4 hours to remove moisture and then the reactor was cooled to room temperature. Polyethylene glycol monomethyl ether and the same amount of ε-caprolactone were added to the reactor in a nitrogen atmosphere, followed by vacuum drying at 60° C. for 1 hour. The reactor was gradually heated to 130° C. in a nitrogen atmosphere, reacted for 18 hours, and cooled to room temperature to terminate the reaction. To the reactor cooled to room temperature, methylene chloride was added to dissolve the reactant, and then slowly added to the excess amount of cold ethyl ether to precipitate the copolymer. The precipitated block copolymer was filtered and then vacuum-dried at 40° C. for 48 hours to finally obtain a polyethylene glycol (A)-polycaprolactone (B) copolymer (P5).

Comparative Example 2: Production of Amphiphilic Polymer (P6)

A polyethylene glycol (A)-polycaprolactone (B) copolymer (P6) was synthesized in the same manner as in Comparative Example 1 and produced, except that a double amount of ε-caprolactone relative to polyethylene glycol monomethyl ether was added upon synthesizing the copolymer.

Comparative Example 3: Production of Amphiphilic Polymer (P7)

After dissolving a polyethylene glycol monomethyl ether polymer (molecular weight: 5,000, manufacturer: Aldrich) forming the first block in dichloromethane at a concentration of 30%, 3 equivalents of triethylamine and 2 equivalents of 2-bromoisobutyryl bromide relative to the —OH functional group are added thereto and reacted to prepare an initiator for ATRP. Thereafter, a process of precipitation and collection in a solvent of diethyl ether is repeated twice and dried to obtain a bromine-terminal polyethylene glycol polymer from which impurities have been removed. 100 parts by weight of the obtained bromine-terminal polyethylene glycol polymer was dissolved in 250 parts by weight of an anisole reaction solvent on a flask and 150 parts by weight of methyl methacrylate was introduced and the flask was sealed with a rubber stopper. Thereafter, the dissolved oxygen was removed through nitrogen purging and stirring at room temperature for 30 minutes, the flask was immersed in an oil bath set at 60° C., and the reaction was carried out by introducing a cupric bromide complex and a catalyst reducing agent. When the desired molecular weight was prepared, the reaction was terminated to prepare an amphiphilic polymer.

Comparative Example 4: Production of Amphipathic Polymer (P8)

2.5 parts by weight of NaH relative to 5 parts by weight of TEMPO ((2,2,6,6-tetramethyl-piperidin-1-yeoxyl) is dissolved in DMF (dimethylformaldehyde) at a concentration of 10%, stirred for 1 hour under reflux, and then 100 parts by weight of a bromine-terminal polyethyleneglycol monomethylether (prepared in Example 1) polymer dissolved in DMF (dimethylformaldehyde) at a concentration of 20% is dropped. After stirring for 24 hours under reflux, the excess amount of NaH is removed by dropping methanol, and then a process of precipitation and collection in a solvent of diethyl ether is repeated twice and dried to obtain an alkoxy amine-terminal polyethylene glycol polymer from which impurities have been removed. The above-prepared alkoxy amine-terminal polyethyleneglycol monomethyl ether polymer was dissolved in an anisole reaction solvent on a flask and styren (B1) was introduced and the flask was sealed with a rubber stopper. Thereafter, the dissolved oxygen was removed through nitrogen purging and stirring at room temperature for 30 minutes, the flask was immersed in an oil bath set at 120° C., and the reaction was carried out. When the desired molecular weight was prepared, the reaction was terminated to prepare an amphiphilic polymer.

Experimental Example 1—Evaluation of Block Ratio and Molecular Weight of the Produced Amphiphilic Polymer The block ratio and the molecular weight of the produced amphiphilic polymers (P1-P8) were evaluated by the following methods and shown in Table 1.

Specifically, the polymer solution was solidified through a purification step of the polymer solution in which the catalyst was completely removed and then the block ratio of the amphiphilic polymer was confirmed through $^1$H NMR analysis. In the purification of the polymer solution, the polymer solution is solidified by passing it through an alumina column to remove the copper complex catalyst or dropping it to hexane with stirring in the absence of the step to remove the residual monomers. The solidified polymer is dried in a vacuum oven for 24 hours. The amphiphilic polymer purified by the above method is dissolved in a solvent of CDCl$_3$ and measured with a $^1$H NMR analysis instrument.

As an analytical result of Examples 1 to 4, no 1H peak derived from CH$_2$=C(CH$_3$)— of the methylmethacrylate double bond terminal was confirmed, and no 1H peak derived from CH$_2$=C— of the vinyl monomer was also confirmed. Accordingly, it can be confirmed that no unreacted monomer is present.

Also, in the case of Examples 1 to 4 and Comparative Examples 1 to 4, since 3H peaks derived from —OCH$_3$ of the ethylene glycol block terminal were confirmed at around 3.2 ppm, and the ratio and molecular weight of each polymer block were calculated, based on the above. Since peaks of about 450 H (4H X repeating units: 113) derived from —CH$_2$CH$_2$O— of ethylene glycol formed into the polymer appeared in the region of 3.6-3.8 ppm, and in the case of Examples 1 to 4 and Comparative Examples 3 and 4, 3H peaks derived from —CH$_3$ adjacent to the main chain of methyl methacrylate formed into the polymer appeared in the region of 3.5-3.6 ppm and 4H to 8H peaks derived from benzene rings of the side chain formed into the polymer appeared in the region of 7.2 ppm or less, the content of each constituent monomer was calculated as a mass fraction through an area ratio thereof.

In the case of Comparative Examples 1 and 2, since 2H peaks derived from the first —CH$_2$— on the right of —CO— in —(COCH$_2$CH$_2$CH$_2$CH$_2$CH$_2$—O)$_n$—, which is a chain of caprolactone formed into the polymer, appeared in the region of 2.3-2.4 ppm, the molecular weight was confirmed through the 3H peak area derived from —OCH$_3$ of the ethylene glycol terminal and the 2H peak area derived from the first —CH$_2$— on the right of —CO— of caprolactone.

TABLE 1

| | Molecular Weight (Mn, A:B) | Block Ratio (A:B) | Weight Ratio of Second Block Polymerized Units (B1:B2) |
|---|---|---|---|
| Example 1 | 11,000 (5000:6000) | 4.55:5.45 | 10:90 |
| Example 2 | 11,000 (5000:6000) | 4.55:5.45 | 10:90 |
| Example 3 | 11,000 (5000:6000) | 4.55:5.45 | 30:70 |
| Example 4 | 11,000 (5000:6000) | 4.55:5.45 | 50:50 |
| Comparative Example 1 | 9,900 (5000:4900) | 5.05:4.95 | — |
| Comparative Example 2 | 14,700 (5000:9700) | 3.40:6.60 | — |
| Comparative Example 3 | 10,500 (5000:5500) | 4.76:5.24 | — |
| Comparative Example 4 | 11,000 (5000:6000) | 4.55:5.45 | — |

Experimental Example 2—Preparation of Micelle and Measurement of Turbidity

Genistein as a poorly soluble material was encapsulated using the synthesized amphiphilic polymer (P1 to P8). First, a solution of 10 g of the amphiphilic polymer dissolved in 30 mL of ethanol was mixed with a solution of 2 g of genistein dissolved in 20 g of dipropylene glycol (DPG). The solution was slowly added to 100 mL of an aqueous solution of 0.5% polyvinyl alcohol while stirring. After being left while stirring for a certain period of time to evaporate the solvent of ethanol, the solution was prepared to have a genistein content of 2%, by removing the residual ethanol using a rotary evaporator. The prepared solution was diluted with 10 times of purified water and then stored at room temperature (25° C.) for 7 days, and the change over time was confirmed by a turbidity measurement and shown in Table 3. It was measured using Turbiscan from Formulaction Co., Ltd., and the upper liquid of the solution stored for 7 days was sampled to measure transmittance, and the turbidity was shown by the following equation 1.

$$\text{Turbidity} = \log(1/(\text{transmittance}(T))) \quad \text{[Equation 1]}$$

TABLE 2

| | Example | | | | Comparative Example | | | |
|---|---|---|---|---|---|---|---|---|
| | 1 | 2 | 3 | 4 | 1 | 2 | 3 | 4 |
| 0 day | 0.137 | 0.201 | 0.215 | 0.2 | 0.155 | 0.125 | 0.09 | 0.13 |
| 7 day after | 0.129 | 0.227 | 0.282 | 0.192 | 0 | 0 | 0.05 | 0.05 |

Through the turbidity measurement of the micelle solution, the change over time in the sample was confirmed, and in the case of Comparative Examples, it could be confirmed that the stabilization of the capsules was decreased due to the agglutination of the drug, and thus all the capsules sank after 7 days.

Experimental Example 3—Confirmation of Dissolution Concentration of Drug

The solution prepared to have a genistein content of 2% in Experimental Example 2 above was diluted with 10 times of purified water and filtered with a syringe filter (pore size: 1 μm) to remove the precipitated genistein, and then the content of genistein encapsulated in the amphiphilic polymer micelle particles was measured from liquid chromatography (HPLC). Drug loading capacity and drug loading efficiency of the amphiphilic polymer were calculated by the following equations and the particle size of the micelle particles containing the amphiphilic polymer in which the drug was collected was measured using Zetasizer 3000 from Malvern Ltd.

$$\text{Drug loading capacity} = \frac{\text{Drug impregnation amount}}{\text{Drug impregnation amount} + \text{Bolock copolymer content}} \times 100 \ (\%) \quad \text{[Equation 2]}$$

$$\text{Drug loading efficiency} = \frac{\text{Drug impregnation amount}}{\text{Initial drug input}} \times 100 \ (\%) \quad \text{[Equation 3]}$$

TABLE 3

| | Example | | | | Comparative Example | | | |
|---|---|---|---|---|---|---|---|---|
| | 1 | 2 | 3 | 4 | 1 | 2 | 3 | 4 |
| Particle size (diameter, nm) | 190 | 250 | 265 | 205 | 100 | 150 | 110 | 160 |
| Loading capacity (%) | 16.5 | 18.9 | 15.8 | 15 | 1.2 | 1.8 | 2.4 | 2.2 |
| Loading efficiency (%) | 82 | 96 | 78 | 80 | 6 | 9 | 13 | 9 |

EXPLANATION OF REFERENCE NUMERALS

100: drug
200: amphiphilic polymer
201: first block
202: second block

The invention claimed is:
1. An amphiphilic polymer comprising:
   a first block (A) comprising a polymer having a solubility parameter of 10 $(\text{cal/cm}^3)^{1/2}$ or more; and
   a second block (B) phase-separated from said first block (A) and comprising a polymerized unit (B1) of a polymerizable monomer satisfying Formula 1 and a polymerized unit (B2) of an acrylic monomer or vinyl monomer having a solubility parameter of a single polymer of less than 10 $(\text{cal/cm}^3)^{1/2}$:

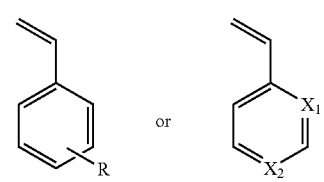

[Formula 1]

wherein, R is a functional group capable of forming a hydrogen bond, or an alicyclic hydrocarbon group or aromatic substituent group comprising a functional group capable of forming a hydrogen bond, where said functional group is at least one selected from the group consisting of a hydroxyl group, an amine group, a nitro group, an imide group, an alkoxysilane group and a cyano group, and $X_1$ and $X_2$ are each independently carbon or nitrogen.

2. The amphiphilic polymer according to claim 1, wherein said first block (A) is any one selected from the group consisting of polyethylene glycol, a polyethylene glycol-propylene glycol copolymer, polyvinyl pyrrolidone and polyethyleneimine.

3. The amphiphilic polymer according to claim 1, wherein said acrylic monomer is a compound represented by Formula 2 or Formula 3:

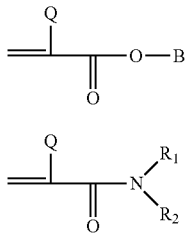

[Formula 2]

[Formula 3]

wherein, Q is hydrogen or an alkyl group, and B in Formula 2 is a linear or branched alkyl group, an alicyclic hydrocarbon group, an aromatic substituent group or a carboxyl group, having at least 1 carbon atom and $R_1$ and $R_2$ in Formula 3 are each independently hydrogen, a linear or branched alkyl group, an alicyclic hydrocarbon group or an aromatic substituent group, having at least 1 carbon atom.

4. The amphiphilic polymer according to claim 3, wherein, in Formula 2, Q is hydrogen or an alkyl group having 1 to 4 carbon atoms, and B is an alkyl group having at least 1 carbon atom or an alicyclic hydrocarbon group having 6 to 12 carbon atoms.

5. The amphiphilic polymer according to claim 1, wherein said vinyl monomer is represented by Formula 4 or Formula 5:

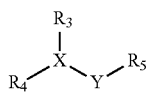

[Formula 4]

wherein, X is a nitrogen atom or an oxygen atom, Y is a carbonyl group or a single bond, $R_3$ and $R_5$ are each independently hydrogen or an alkyl group, or $R_3$ and $R_5$ are linked together to form an alkylene group, and $R_4$ is an alkenyl group (provided that when X is an oxygen atom, R3 is not present);

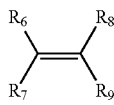

[Formula 5]

wherein, $R_6$, $R_7$ and $R_8$ are each independently hydrogen or an alkyl group, and $R_9$ is a cyano group or an aromatic substituent group.

6. The amphiphilic polymer according to claim 1, wherein the polymerized unit (B1) of the polymerizable monomer satisfying Formula 1 and the polymerized unit (B2) of the acrylic monomer or vinyl monomer having a solubility parameter of a single polymer of less than 10.0 $(cal/cm^3)^{1/2}$ in said second block (B) have a weight ratio (B1:B2) in a range of 0.5:99.5 to 50:50.

7. The amphiphilic polymer according to claim 6, wherein the polymerized unit (B1) of the polymerizable monomer satisfying Formula 1 and the polymerized unit (B2) of the acrylic monomer or vinyl monomer having a solubility parameter of a single polymer of less than 10.0 $(cal/cm^3)^{1/2}$ in said second block (B) have a weight ratio (B1:B2) in a range of 1:99 to 30:70.

8. The amphiphilic polymer according to claim 1, wherein said first block (A) and said second block (B) have a block ratio (A:B) different from each other.

9. The amphiphilic polymer according to claim 1, wherein said first block (A) and said second block (B) have a block ratio (A:B) of 1:9 to 9:1.

10. The amphiphilic polymer according to claim 9, wherein said first block (A) and said second block (B) have a block ratio (A:B) of 3:7 to 7:3.

11. Micelles comprising the amphiphilic polymer of claim 1.

12. The micelles according to claim 11, further comprising a drug encapsulated by said amphiphilic polymer.

13. The micelles according to claim 12, wherein the second block (B) of said amphiphilic polymer is adjacent to the drug.

14. The micelles according to claim 11, having an average particle diameter in a range of 1 nm to 10,000 nm.

15. The micelles according to claim 12, wherein said drug comprises a physiologically active substance.

16. The micelles according to claim 15, wherein said physiologically active substance is poorly soluble.

17. The micelles according to claim 16, wherein said physiologically active substance is any one selected from the group consisting of genistein, daidzein, cucurbitacin, prangenidin or a derivative thereof; and a mixture thereof.

18. A composition for producing particles, comprising the micelles of claim 11.

19. The composition according to claim 18, wherein said micelles further comprise a drug encapsulated by the amphiphilic polymer.

20. The micelles according to claim 16, wherein said physiologically active substance is polyphenols.

* * * * *